United States Patent
Zhu et al.

(10) Patent No.: US 10,750,947 B2
(45) Date of Patent: Aug. 25, 2020

(54) SYSTEM AND METHOD FOR INTRAOPERATIVE FLUORESCENCE IMAGING IN AMBIENT LIGHT

(71) Applicant: BOARD OF REGENTS OF THE UNIVERSITY OF TEXAS SYSTEM, Austin, TX (US)

(72) Inventors: Banghe Zhu, Sugar Land, TX (US); Eva M. Sevick-Muraca, Montgomery, TX (US); John C. Rasmussen, Spring, TX (US)

(73) Assignee: Board of Regents of the University of Texas System, Austin, TX (US)

( * ) Notice: Subject to any disclaimer, the term of this patent is extended or adjusted under 35 U.S.C. 154(b) by 1083 days.

(21) Appl. No.: 15/110,547

(22) PCT Filed: Jan. 8, 2015

(86) PCT No.: PCT/US2015/010588
§ 371 (c)(1),
(2) Date: Jul. 8, 2016

(87) PCT Pub. No.: WO2015/105951
PCT Pub. Date: Jul. 16, 2015

(65) Prior Publication Data
US 2016/0324420 A1    Nov. 10, 2016

Related U.S. Application Data

(60) Provisional application No. 61/924,950, filed on Jan. 8, 2014.

(51) Int. Cl.
*A61B 5/00* (2006.01)
*A61B 1/04* (2006.01)
(Continued)

(52) U.S. Cl.
CPC ............ *A61B 5/0035* (2013.01); *A61B 1/043* (2013.01); *A61B 1/313* (2013.01); *A61B 5/0071* (2013.01);
(Continued)

(58) Field of Classification Search
CPC ... A61B 5/0035; A61B 5/0084; A61B 5/7221; A61B 1/043; A61B 1/313; A61B 5/0071;
(Continued)

(56) References Cited

U.S. PATENT DOCUMENTS 7,599,732 B2 *  10/2009  Sevick-Muraca .... A61B 5/0059
                                                  356/301
2005/0085732 A1   4/2005  Sevick-Muraca et al.
(Continued)

OTHER PUBLICATIONS

International Patent Application No. PCT/US2015/010588 International Search Report and Written Opinion dated Apr. 30, 2015 (14 pages).

*Primary Examiner* — Joel Lamprecht
(74) *Attorney, Agent, or Firm* — Blank Rome LLP

(57) ABSTRACT

A system and method for intraoperative fluorescence imaging. A system for intraoperative fluorescence imaging includes a visible light source, a laser light source, a visible light image detector, a fluorescence image detector, radio frequency (RF) circuitry, and an image processing system. The RF circuitry is coupled to the laser light source and the fluorescence image detector. The RF circuitry is configured to modulate laser light generated by the laser source, and modulate an intensifier of the fluorescence image detector. The image processing system is coupled to the visible light image detector and the fluorescence image detector. The image processing system is configured to merge a fluorescence image produced by the fluorescence image detector and a visible light image produced by the visible light image detector to generate an intraoperative image showing an
(Continued)

outline of a region of interest identified in the fluorescence image overlaid on the visible light image.

22 Claims, 4 Drawing Sheets

(51) Int. Cl.
*A61B 1/313* (2006.01)
*G06K 9/32* (2006.01)
*G06T 5/50* (2006.01)
*A61B 6/00* (2006.01)
*A61B 90/00* (2016.01)
*H04N 5/369* (2011.01)

(52) U.S. Cl.
CPC .......... *A61B 5/0084* (2013.01); *A61B 5/0086* (2013.01); *A61B 5/7221* (2013.01); *A61B 5/7425* (2013.01); *A61B 6/00* (2013.01); *A61B 90/37* (2016.02); *G06K 9/3233* (2013.01); *G06T 5/50* (2013.01); *H04N 5/369* (2013.01); *A61B 2090/365* (2016.02); *A61B 2505/05* (2013.01); *A61B 2576/00* (2013.01); *G06T 2207/10024* (2013.01); *G06T 2207/10064* (2013.01); *G06T 2207/20221* (2013.01)

(58) Field of Classification Search
CPC .............. A61B 2576/00; A61B 5/7425; A61B 2090/365; A61B 90/37; A61B 2505/05; A61B 5/0086; A61B 6/00; H04N 5/369; G06K 9/3233; G06T 5/50; G06T 2207/10024; G06T 2207/10064; G06T 2207/20221
See application file for complete search history.

(56) References Cited

U.S. PATENT DOCUMENTS

| | | |
|---|---|---|
| 2006/0264761 A1 | 11/2006 | Knoche et al. |
| 2009/0236541 A1 | 9/2009 | Lomnes et al. |
| 2010/0220903 A1 | 9/2010 | May et al. |
| 2013/0335819 A1 | 12/2013 | Cooper |

* cited by examiner

SYSTEM AND METHOD FOR INTRAOPERATIVE FLUORESCENCE IMAGING IN AMBIENT LIGHT

CROSS REFERENCE TO RELATED APPLICATIONS

This application is a 35 U.S.C. § 371 national stage application of PCT/US2015/010588 filed Jan. 8, 2015, and entitled "System and Method for Intraoperative Fluorescence Imaging in Ambient Light," which claims the benefit of U.S. provisional application Ser. No. 61/924,950, filed on Jan. 8, 2014, entitled "System and Method for Intraoperative Fluorescence Imaging in Ambient Light," each of which is hereby incorporated herein by reference in its entirety.

GOVERNMENT LICENSE RIGHTS

This invention was made with government support under CA136404 and CA128919 awarded by National Institutes of Health. The government has certain rights in the invention.

BACKGROUND

Although much progress has been made to develop effective new cancer therapeutics, surgery remains the foundation of cancer treatment for either complete resection of primary lesions or for debulking (or cytoreductive surgery) that enables more efficacious radiation and/or chemotherapy. Residual tumor burden after surgery is strongly correlated with reduced survivor rates. When possible, wide-field surgical excision can reduce the chance of positive tumor margins and residual disease, although it can also lead to disfigurement and enhanced risk for surgical morbidities. Despite the crucial role that surgery plays in outcomes, tissue resection is predominantly guided through visual cues that can be augmented by tactile cues in the setting of open surgery. With the increasing use of robotic, laproscopic, and/or endoscopic surgeries, tactile cues become limited.

Fluorescence imaging with molecularly targeted agents provides the "low hanging fruit" of molecular medicine by adding molecular diagnostics and potentially improving surgery by reducing the amount of residual disease left behind. Fluorescence molecular imaging involves the administration of a targeted-agent labeled with a fluorophore. While the development of fluorescence imaging agents is the subject of several academic laboratories, there remains a need for instrumentation that can sensitively detect the fluorescence associated with disease markers that demarks disease at pM-fM tissue concentrations. In the operating room, backscattered excitation light and ambient room light can "leak" through filters and reduce the contrast that is necessary for visual delineation of tumor boundaries. In current practice, using laproscopic and endoscopic surgical tools, fluorescence imaging concurrent with white light illumination of the surgical field is necessary for fluorescence molecularly guided resection, yet the white light illumination of current laproscopic/endoscopic devices causes "leakage" through filters also reducing contrast. In order to achieve molecularly guided surgery, procedures should be conducted simultaneously with diagnostic imaging to be effective.

SUMMARY

A system and method for intraoperative fluorescence imaging are disclosed herein. In one embodiment, a system for intraoperative fluorescence imaging includes a visible light illumination source, a laser light source, a visible light image detector, a fluorescence image detector, radio frequency (RF) circuitry, and an image processing system. The RF circuitry is coupled to the laser light source and the fluorescence image detector. The RF circuitry configured to modulate laser light generated by the laser source, and to modulate an intensifier of the fluorescence image detector. The image processing system is coupled to the visible light image detector and to the fluorescence image detector. The image processing system is configured to merge a fluorescence image produced by the fluorescence image detector and a visible light image produced by the visible light image detector to generate an intraoperative image showing an outline of a region of interest identified in the fluorescence image overlaid on the visible light image.

The RF circuitry may be configured to modulate an intensifier of the fluorescence image detector with as few as three phase delays relative to the modulation of the laser source. In some embodiments, the phase delays may comprise 0°, 90°, and 180°. Each of the phase delays may shifts phase of an RF signal that modulates the intensifier by 90°.

The image processing system may be configured to eliminate non-modulated, visible light from fluorescence images to produce a high contrast fluorescence image using the fluorescence images acquired with the as few as three phase delays. The image processing system may also be configured to merge the high contrast fluorescence image and the visible light image to generate the intraoperative image.

The image processing system may be configured to extract amplitude information from fluorescence images generated at each of the phase delays, to apply a threshold to the amplitude information, and to identify edges of a structure based on the amplitude information above the threshold. The image processing system may also be configured to extract a region of interest corresponding to the identified structures from the visible light image, and merge the edges of the structure with the region of interest extracted from the visible light image.

In another embodiment, a method for intraoperative fluorescence imaging includes illuminating an object with visible light generated by a visible light source, and illuminating the object with laser light generated by a laser light source. The laser light is modulated at a radio frequency. An image of the object is captured via detection of the visible light reflected by the object using a visible light image detector. A fluorescence image of the object is captured, using a fluorescence image detector, via detection of fluorescence generated by the object responsive to the laser light. An intensifier of the fluorescence image detector is modulated at a radio frequency. The fluorescence image and the visible light image are merged to generate an intraoperative image showing an outline of a region of interest identified in the fluorescence image overlaid on the visible light image.

A method may further include modulating the intensifier of the fluorescence image detector with as few as three phase delays relative to the modulation of the laser source. The phase delays may include 0°, 90°, and 180°. Each of the phase delays may shift phase of a radio frequency signal that modulates the intensifier by 90°. Various embodiments may apply different phase delays (i.e., phase delays other than 0°, 90°, and 180°.

A method may also include eliminating non-modulated, visible light from fluorescence images to produce a high contrast fluorescence image using the fluorescence images acquired with the as few as three phase delays. The high contrast fluorescence image and the visible light image may be merged to generate the intraoperative image.

A method may additionally include extracting amplitude information from fluorescence images generated at each of the phase delays, applying a threshold to the amplitude information, and identifying edges of a structure based on the amplitude information above the threshold. A region of interest corresponding to the identified structures may be extracted from the visible light image, and the edges of the structure merged with the region of interest extracted from the visible light image.

In a further embodiment, apparatus for intraoperative fluorescence imaging includes a radio frequency (RF) oscillator, a phase shifter, a white light source, a visible light image detector, a laser light source, a fluorescence image detector, and a control and image acquisition system. The phase shifter is coupled to an output of the radio frequency oscillator. The laser light source is coupled to the RF oscillator. RF signal generated by the RF oscillator modulates laser light generated by the laser light source. The fluorescence image detector includes an intensifier. The intensifier is coupled to the phase shifter and phase shifted RF signal output by the phase shifter modulates the intensifier. The control and image acquisition system is coupled to the visible light image detector and to the fluorescence image detector. The image processing system is configured to merge a fluorescence image produced by the fluorescence image detector and a visible light image produced by the visible light image detector to generate an intraoperative image showing an outline of a region of interest identified in the fluorescence image overlaid on the visible light image. The image processing system is also configured to set the phase shifter to modulate the intensifier of the fluorescence image detector with as few as three phase delays relative to the modulation of the laser source per intraoperative image.

The control and image acquisition system may be configured to set each successive phase delay to advance phase of the RF signal that modulates the intensifier by 90 degrees.

The control and image acquisition system may be configured to eliminate non-modulated, visible light from fluorescence images to produce a high contrast fluorescence image using the fluorescence images acquired with the as few as three phase delays, and to merge the high contrast fluorescence image and the visible light image to generate the intraoperative image.

The control and image acquisition system may be configured to extract amplitude information from fluorescence images generated at each of the phase delays, apply a threshold to the amplitude information, identify edges of a structure based on the amplitude information above the threshold, extract a region of interest corresponding to the identified structures from the visible light image, and merge the edges of the structure with the region of interest extracted from the visible light image.

In some embodiments, a system for intraoperative fluorescence imaging includes a visible light illumination source, a laser light source, a visible light image detector, a fluorescence image detector, radio frequency (RF) circuitry, and an image processing system. The RF circuitry is coupled to the laser light source and the fluorescence image detector. The RF circuitry configured to modulate laser light generated by the laser source. The image processing system is coupled to the visible light image detector and to the fluorescence image detector. The image processing system is configured to merge a fluorescence image produced by the fluorescence image detector and a visible light image produced by the visible light image detector to generate an intraoperative image showing an outline of a region of interest identified in the fluorescence image overlaid on the visible light image.

The RF circuitry may be configured to modulate the laser light source with as few as two phase delays, wherein lasing current is below and above a lasing threshold of the laser light source. The image processing system may configured to eliminate non-modulated, visible light from fluorescence images to produce a high contrast fluorescent image using the fluorescence images acquired with the as few as two phase delays, and to merge the high contrast fluorescent image and the visible light image to generate the intraoperative image.

The image processing system may be configured to extract amplitude information from fluorescence images generated at each of the phase delays, apply a threshold to the amplitude information, and identify edges of a structure based on the amplitude information above the threshold. The image processing system also may be configured to extract a region of interest corresponding to the identified structures from the visible light image, and merge the edges of the structure with the region of interest extracted from the visible light image.

In yet further embodiments, a method for intraoperative fluorescence imaging includes illuminating an object with visible light generated by a visible light source, and illuminating the object with laser light generated by a laser light source. The laser light is modulated at a radio frequency. An image of the object is captured via detection of the visible light reflected by the object using a visible light image detector. A fluorescence image of the object is captured, using a fluorescence image detector, via detection of fluorescence generated by the object responsive to the laser light. The fluorescence image and the visible light image are merged to generate an intraoperative image showing an outline of a region of interest identified in the fluorescence image overlaid on the visible light image.

A method may further include modulating the laser light with as few as two phase delays, wherein lasing current is below and above a lasing threshold of a laser light source generating the laser light. Non-modulated, visible light may be eliminated from fluorescence images to produce a high contrast fluorescent image using the fluorescence images acquired with the as few as two phase delays. The high contrast fluorescence image and the visible light image may be merged to generate the intraoperative image.

A method may additionally include extracting amplitude information from fluorescence images generated at each of the phase delays, applying a threshold to the amplitude information, and identifying edges of a structure based on the amplitude information above the threshold. A region of interest corresponding to the identified structures may be extracted from the visible light image, and the edges of the structure merged with the region of interest extracted from the visible light image.

BRIEF DESCRIPTION OF THE DRAWINGS

For a detailed description of exemplary embodiments of the invention, reference will now be made to the accompanying drawings in which.

NOTATION AND NOMENCLATURE

Figure 1:
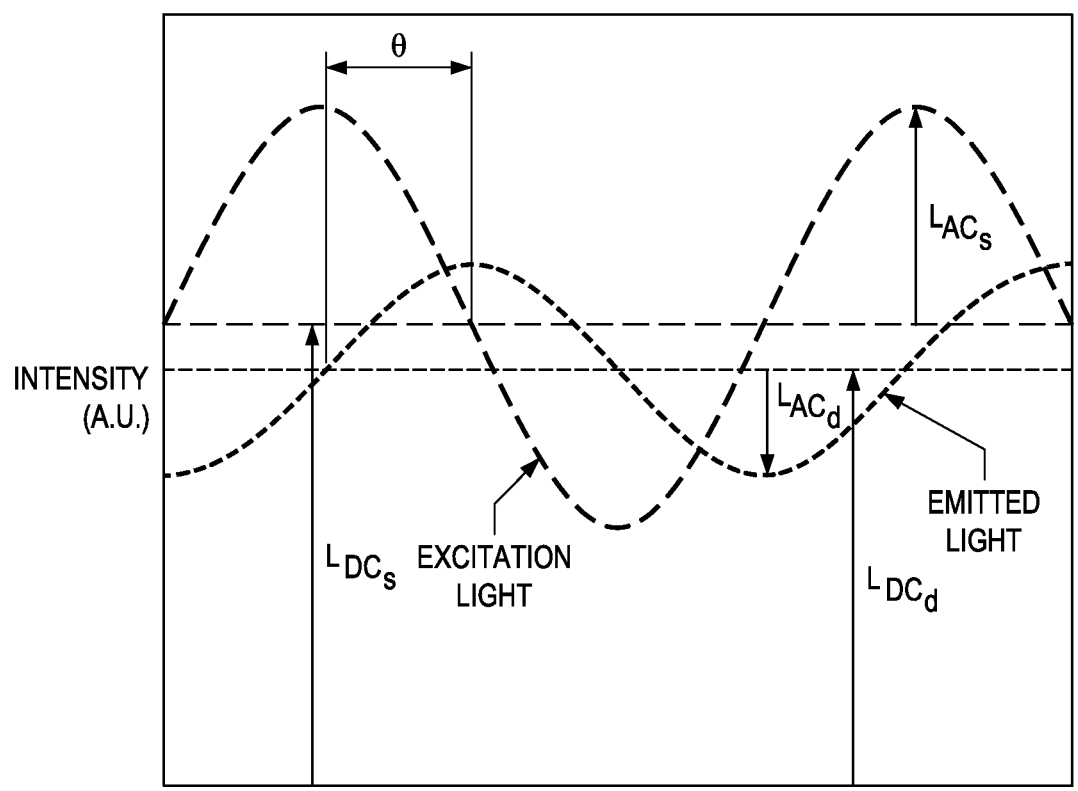
FIG. 1 shows a diagram of signals for frequency domain measurement suitable for fluorescence imaging in accordance with principles disclosed herein.

Certain terms are used throughout the following description and claims to refer to particular system components. As one skilled in the art will appreciate, companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection, or through an indirect connection via other devices and connections. The recitation "based on" is intended to mean "based at least in part on." Therefore, if X is based on Y, X may be based on Y and any number of other factors.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Conventional charge coupled device (CCD) or complementary metal oxide semiconductor (CMOS) camera based fluorescence imaging systems for intraoperative image-guided tumor detection employ continuous wave (CW) image acquisition due to its low cost and simple implementation. Although the strong backscattered excitation light can be minimized by use of optimized filtration schemes, the operating room light can decrease the contrast between a tumor and normal tissue, resulting in inaccuracy in tumor margin determination. In contrast, a frequency domain (FD) based optical imager can be operated in a non-light-tight environment because the amplitude of the detected fluorescence is insensitive to the ambient light.

In one imaging system, a Gen III image intensifier is adapted to a CCD or CMOS image sensor to electronically amplify (near infra-red fluorescence) NIRF signals (with gains as much as $10^6$) and to convert them into green (550 nm) phosphor signals that can be collected by a conventional integrating CCD or CMOS image sensor. Due to the fast response time of the photocathode, the photocathode of the image intensifier and the excitation light source (e.g., a laser diode) may be modulated at MHz frequencies to conduct frequency-domain (FD) measurements and NIRF tomography of interior tissues contrasted by a NIRF molecular imaging agent. During data acquisition, the phase of the intensifier modulation is evenly stepped, or delayed, N (N=32 or 64) times between 0 and 360 degrees relative to the phase of the laser diode modulation. At each phase delay, a phase-sensitive image is acquired by the CCD or CMOS camera for a given exposure time. A fast Fourier transform (FFT) is performed to calculate phase, and modulation amplitude for tomography. In such a system, the data acquisition and computation may require several minutes, making the system impractical for use in intraoperative fluorescence imaging.

Embodiments of the present disclosure include a fast intensified charge-coupled device (ICCD or ICMOS) based frequency domain phase modulation (FDPM) imager for intraoperative fluorescence-guided surgery.

Embodiments disclosed herein employ a frequency-domain based measurement approach with a light source that is intensity modulated at radio frequencies (RF) wherein (i) the minimum and maximum laser diode driving current are above the threshold for diode lasing, or (ii) the minimum laser diode driving current is is below and the maximum laser diode driving current is above the threshold. As the intensity-modulated light propagates through the high scattering tissue, the light is amplitude attenuated and phase-shifted relative to incident light. Before reaching detectors, generated fluorescence is further attenuated and phase-shifted as a result of the quantum efficiency, lifetime of the fluorochrome, and absorption and scattering properties of the intervening tissue.

FIG. 1 shows excitation input and detected fluorescent signals for frequency domain measurement in accordance with various embodiments wherein the minimum and maximum laser diode driving current are above the threshold for diode lasing. With emitted light L(x,y) from the tissue or phantom surface that reaches the photocathode of an image intensifier having a phase delay, θ(x,y); average intensity, $L_{DC}(x,y)$; and amplitude intensity $L_{AC}(x,y)$ at the modulation frequency co:

$$L(x,y)=L_{DC}(x,y)+L_{AC}(x,y)\cos[\omega t+\theta(x,y)] \quad (1)$$

The modulated gain of the image intensifier includes DC and AC components denoted by $G_{DC}$ and $G_{AC}$, respectively, and an additional phase delay $\theta_{inst}$ induced by the instrument response time at the modulation frequency:

$$G=G_{DC}+G_{AC}\cos(\omega t+\theta_{inst}) \quad (2)$$

The resulting signals (S), prior to striking the phosphor screen, are a product of L(x,y) and G, and contains both high frequency and low frequency signals:

$$S(x,y) = \quad (3)$$
$$L(x,y) \times G = L_{DC}(x,y) \cdot G_{DC} + L_{DC}(x,y) \cdot G_{AC}\cos[\omega t + \theta_{instr} + \eta] +$$
$$G_{DC} \cdot L_{AC}(x,y)\cos[\omega t + \theta(x,y)] +$$
$$\frac{L_{AC}(x,y)G_{AC}}{2}\cos(-\theta(x,y) + \theta_{inst} + \eta) +$$
$$\frac{L_{AC}(x,y) \cdot G_{AC}}{2}\cos[2\omega t + \theta_{inst} + \theta(x,y)]$$

Because the response time of the phosphor screen is sub-milliseconds (ms), the high frequency signals are automatically filtered out and the low frequency signals registered on the CCD camera are simply:

$$S(x,y)=DC(x,y)+AC(x,y)\cos(-\theta(x,y)+\theta_{inst}+\eta) \quad (4)$$

where:

$$DC(x,y)=L_{DC}(x,y) \cdot G_{DC};$$

$$AC(x,y) = \frac{L_{AC}(x,y)G_{AC}}{2};$$

and $\eta$ is the phase lag between the modulation of the laser diode and the image intensifier.

Embodiments may acquire as few as three images taken with specific phase delays, r, denoted here as:

$$S_0=S(x,y,\eta=0°),$$

$$S_{90}=S(x,y,\eta=90), \text{ and}$$

$$s_{180}=S(x,y,\eta=1800)$$

In this example, using the optimal 90 degree phase-shift between acquired, sequential images, the relative AC(x,y) amplitude of detected signals can be recovered using the following equation:

$$AC(x,y)=\tfrac{1}{2}\sqrt{(2S_{90}-S_0-S_{180})^2+(S_{180}-S_0)_2} \quad (5)$$

Figure 2:
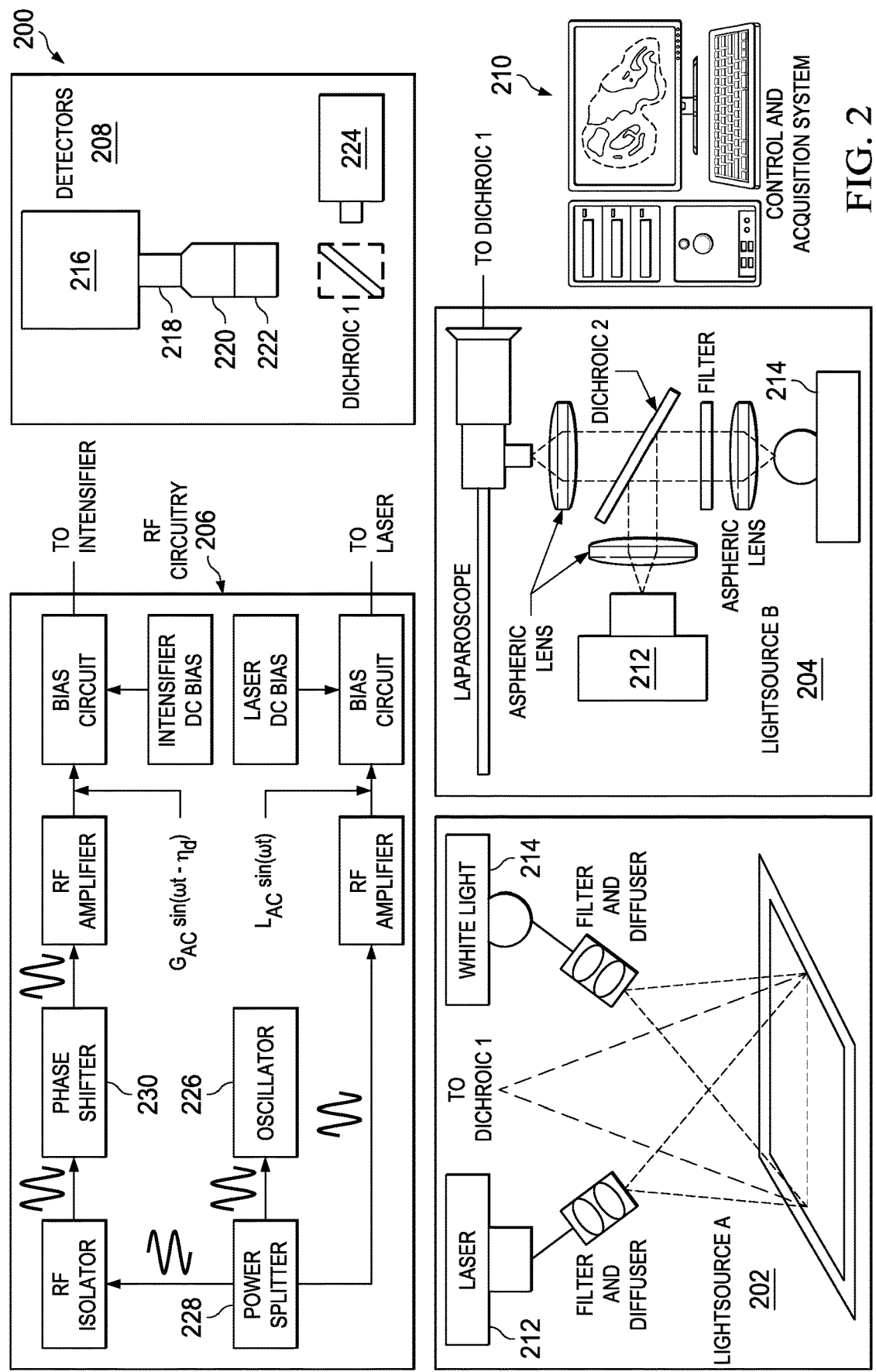
FIG. 2 shows a block diagram of a system 100 for intraoperative fluorescence imaging in ambient light using frequency-domain measurement in accordance with principles disclosed herein.

FIG. 2 shows a schematic diagram of an ICCD based FD fluorescence imaging system for image-guided surgery in accordance with various embodiments. The system 200 includes light source A 202, light source B 204, RF circuitry 206, detector 208, control and acquisition system 210, and at least one of light source A 202 and light source B 204. The light sources A and B are designed for open surgery and laparoscopic surgery, respectively, where the laser source 212 is used for excitation of fluorophores or fluorescent protein and the white light source 214 is used for color imaging. The light source output is expanded to illuminate the tissue surface or collimated by aspheric lenses into a light guide for internal tissue illumination. The selection of laser diode, filters and dichroic mirrors is based on the excitation and emission spectra of fluorophore and/or fluorescent gene reporter.

The detector 208 includes an ICCD camera 216, an intensifier 218, a lens 220, filters 222, and a color camera 224. The ICCD camera 216 senses the filtered emitted signals and the color camera 224 is used to record reflected white light.

The RF circuitry 206 includes two outputs for modulating the intensifier 218 and laser source 212 (e.g., a laser diode), respectively. Different modulation frequencies can be used for fluorophores or gene reporter with different lifetimes for maximizing the contrast between a tumor and normal tissues.

The control and acquisition system 210 includes a computing device or other control device that manages and controls the light source A 202, light source B 204, RF circuitry 206, and detector 208, and provides processing of image signals generated by the detector 208. The control and acquisition system 210 also provides processing of imaging signals received from the detector 208. The control and acquisition system 210 may include a processor and a storage device for storing software instructions that are executed by the processor. In some embodiments, the control and acquisition system 210 may be implemented in a computer as is known in the art.

The RF Circuitry 206 includes an RF oscillator 226 and a two-way power splitter 228 that provide simultaneous modulation of the laser source 212 and demodulation of the detected signal at the photocathode of the intensifier 218. A phase-shifter 230 can introduce three phase delays (e.g., 0°, 90°, and 180°) to the RF signal modulating the image intensifier with respect to the laser source signal. To prevent transient noise to laser source control, a unidirectional RF circulator is used to isolate any reflected RF signals due to impedance mismatch from feeding back to the laser source 212. The corresponding RF power of each RF component is calculated and optimized. The characteristics of the laser source 212 are considered in maximizing modulation depths while the resulting optical power delivered to the tissue surface is below the maximum permissible incidence levels established by the Food and Drug Administration (FDA) for clinical applications.

The control and acquisition system 210 causes the light source A 202, light source B 204, RF circuitry 206, and detector 208 to generate laser signals and acquire images at three different phases. Three images acquired at different phase lags (e.g., 0°, 90°, 180°) are stored in memory and transformed into a 2D array by the control and acquisition system 210. The control and acquisition system 210 extracts AC amplitude via pixel manipulation in accordance with equation (5) and applies a selected threshold value to the AC amplitude to remove background noise and tissue autofluorescence. The control and acquisition system 210 identifies tumor margins from the thresholded image using an edge finding function.

To compensate for the different field of view (FOV) of the color image from that of a fluorescence image, the control and acquisition system 210 applies a scale factor to the color image and then trims the same region of interest (ROI) as that of the fluorescence image from the scaled color image for image merging.

The control and acquisition system 210 overlays the edged NIRF image onto the trimmed color image with appropriate opacity (such as 50.0%). The control and acquisition system 210 may display the merged image on a video monitor for guiding a surgeon in removal of the imaged tumor.

Figure 3:
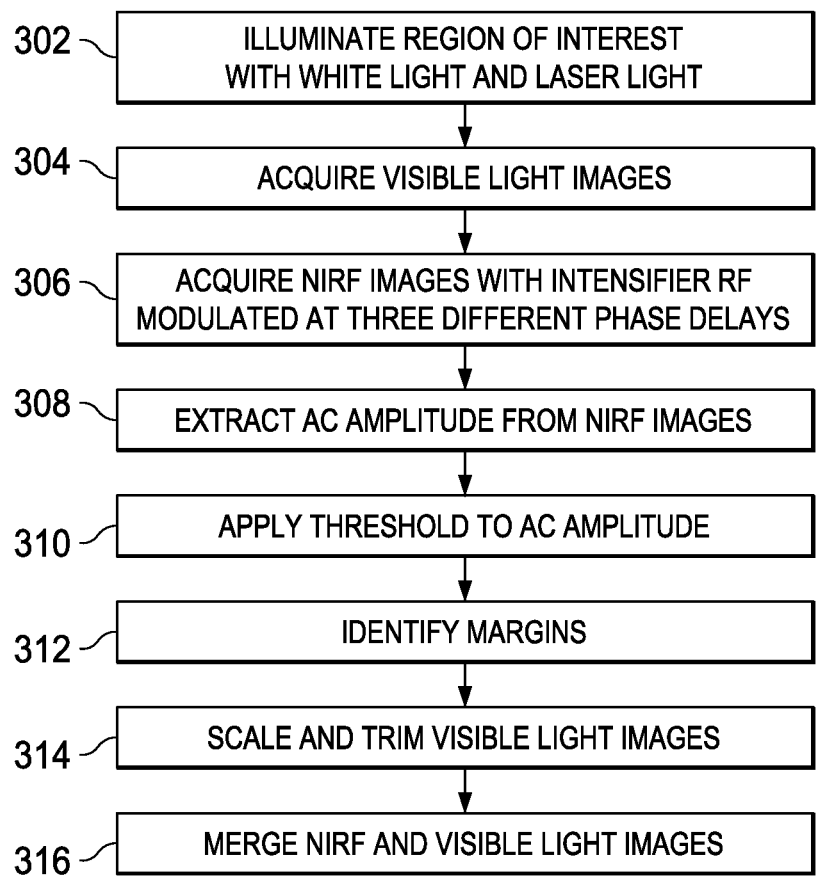
FIG. 3 shows a flow diagram for a method for image processing in accordance with principles disclosed herein.

FIG. 3 shows a flow diagram for a method for image processing in accordance with principles disclosed herein. Though depicted sequentially as a matter of convenience, at least some of the actions shown can be performed in a different order and/or performed in parallel. Additionally, some embodiments may perform only some of the actions shown. In some embodiments, at least some of the operations of FIG. 3, as well as other operations described herein, can be implemented as instructions stored in a computer readable medium and executed by one or more processors.

In block 302, a region of interest (e.g., a region including a tumor) is illuminated with white light generated by the white light source 214 and with laser light generated by the laser light source 212. The laser light is amplitude modulated via the RF circuitry 206.

Figure 4:
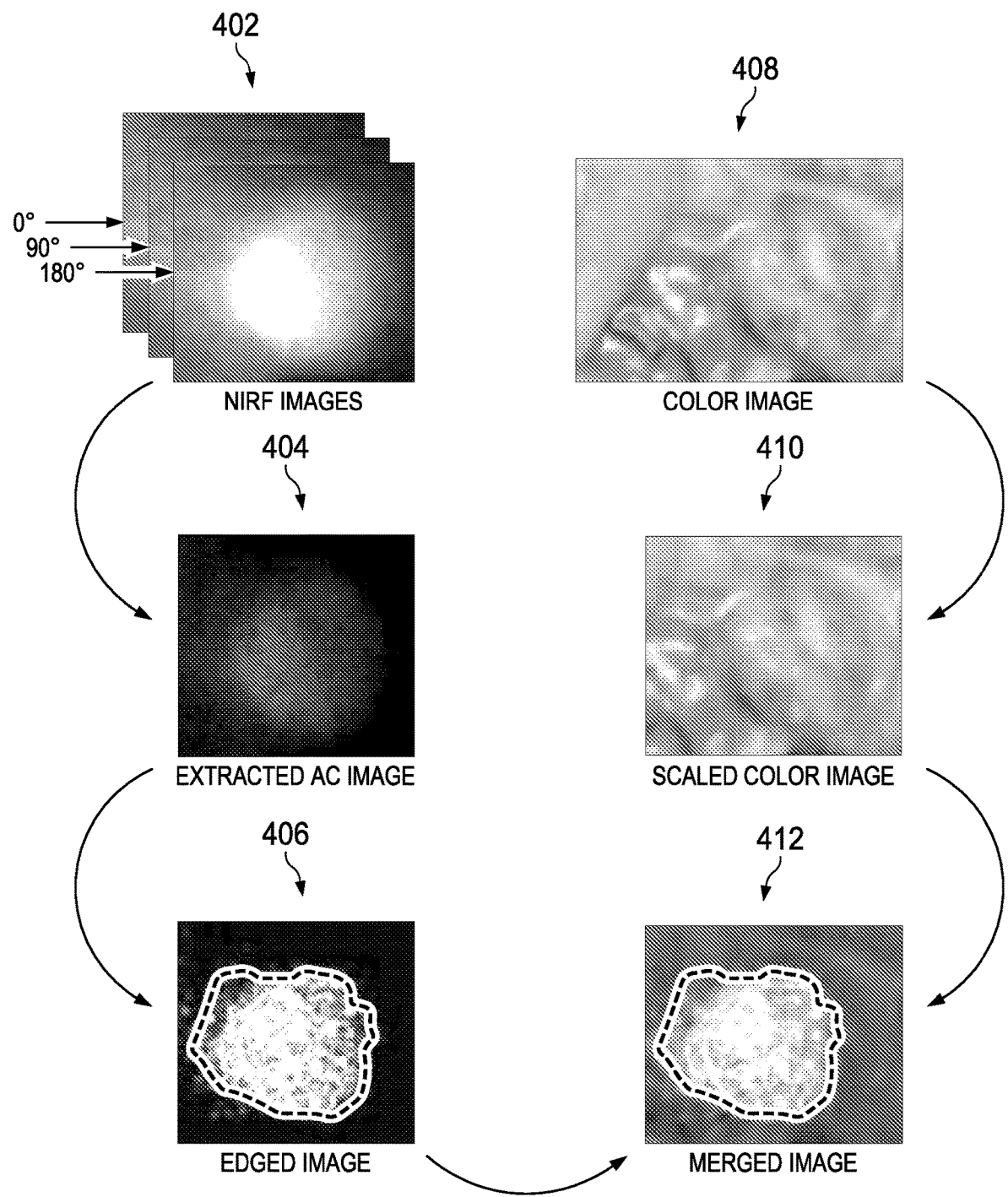
FIG. 4 shows images processed via the method of FIG. 3.

In block 304, the color camera 224 acquires visible light images produced by reflection of the white light by the region of interest. An exemplary visible light image 408 captured by the color camera 224 is shown in FIG. 4.

In block 306, the ICCD camera 206 acquires NIRF images of the light generated by fluorescence of the region of interest. The RF circuitry 206 generates three phases (e.g., 0°, 90°, 180°) of signal that modulate the intensifier 218, and an image is captured by the ICCD camera 206 for each modulation phase. Three exemplary NIRF images 402 acquired at different intensifier phase modulations are shown in FIG. 4.

In block 308, the control and acquisition system 210 extracts AC amplitude from the captured NIRF images. The AC amplitude extraction may be performed in accordance with equation (5). An exemplary AC amplitude image 404 extracted from the NIRF images is shown in FIG. 4.

In block 310, the control and acquisition system 210 applies thresholding to the extracted AC amplitude. Application of a threshold value removes background noise and tissue autofluorescence.

In block 312, the control and acquisition system 210 applies edge detection to identify the margins of the tumor or other structure identified in the NIRF images. An exemplary edged image 406 showing margins of the tumor is shown in FIG. 4.

In block 314, the control and acquisition system 210 applies a scale factor to the visible light images to compensate for the different field of view of the visible light images and the NIRF images. The control and acquisition system 210 trims a region of interest corresponding to the fluorescence images from the scaled visible light images. An exemplary scaled and trimmed visible image 410 of the region of interest is shown in FIG. 4.

In block 316, the control and acquisition system 210 overlays the margined NIRF images onto the scaled, trimmed visible light images to produced merged images that show the outline of the tumor, as detected in the NIRF images, on the visible light images. The merged images may be displayed on a monitor device to guide a surgeon in removal of the tumor. An exemplary merged image 412 is shown in FIG. 4.

Figure 5:
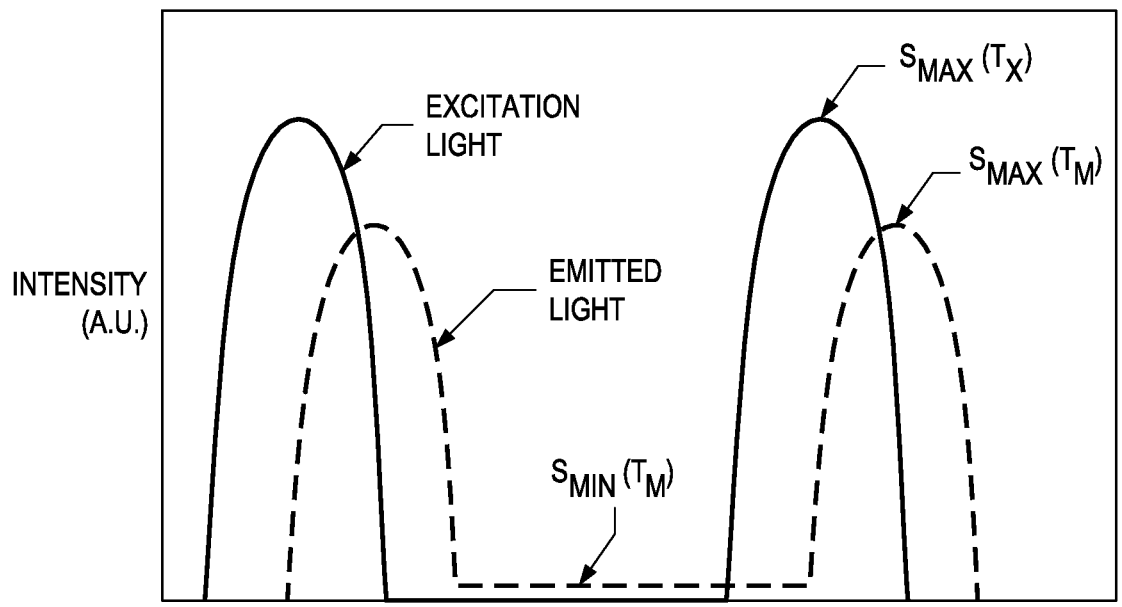
FIG. 5 shows a diagram of signals produced for fluorescence imaging in which the minimum of the modulated laser diode driving current is set below and the maximum laser diode driving current is above the lasing threshold.

In some embodiments, the minimum of the modulated laser diode driving current is set below and the maximum laser diode driving current is above the lasing threshold. FIG. 5 shows an example of signals produced in such embodiments. In this case the gain of the intensification modulation circuit, $G_{AC}$ is zero, the fluorescent signal detected is:

$$S(x,y)=L(x,y) \times G = L_{DC}(x,y) \cdot G_{DC} + G_{DC} \cdot L_{AC}(x,y) \cos[\omega t + (x,y)] \quad (6)$$

and the maximum and minimum signals are:

$$S\max(x,y) = L(x,y) \times G = L_{DC}(x,y) \cdot G_{DC} + G_{DC} \cdot L_{AC}(x,y) \quad (7)$$

$$S\min(x,y) = L(x,y) \times G = 0 \quad (8)$$

By taking the difference between the two maximum and minimum signals, the signals due to fluorescence can be directly attributed to the fluorescent signal.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A system for intraoperative fluorescence imaging, comprising:
   a visible light illumination source;
   a laser light source;
   a visible light image detector;
   a fluorescence image detector;
   radio frequency (RF) circuitry coupled to the laser light source and the fluorescence image detector; the RF circuitry configured to:
      modulate laser light generated by the laser light source; and
      modulate an intensifier of the fluorescence image detector with as few as three phase delays relative to the modulation of the laser light source; and
   an image processing system coupled to the visible light image detector and to the fluorescence image detector, the image processing system configured to:
      merge a fluorescence image produced by the fluorescence image detector and a visible light image produced by the visible light image detector to generate an intraoperative image showing an outline of a region of interest identified in the fluorescence image overlaid on the visible light image; and
      eliminate non-modulated, visible light from fluorescence images to produce a high contrast fluorescent image using the fluorescence images acquired with the as few as three phase delays.

2. The system of claim 1, wherein the phase delays comprise zero degrees, 90 degrees and 180 degrees.

3. The system of claim 1, wherein each of the phase delays shifts phase of an RF signal that modulates the intensifier by 90 degrees.

4. The system of claim 1, wherein the image processing system is configured to merge the high contrast fluorescent image and the visible light image to generate the intraoperative image.

5. The system of claim 1, wherein the image processing system is configured to:
   extract amplitude information from fluorescence images generated at each of the phase delays;
   apply a threshold to the amplitude information; and
   identify edges of a structure based on the amplitude information above the threshold.

6. The system of claim 5, wherein the image processing system is configured to:
   extract a region of interest corresponding to the identified structures from the visible light image; and
   merge the edges of the structure with the region of interest extracted from the visible light image.

7. A method for intraoperative fluorescence imaging, comprising:
   illuminating an object with visible light generated by a visible light source;
   illuminating the object with laser light generated by a laser light source;
   modulating the laser light at a radio frequency;
   capturing, via a visible light image detector, an image of the object via detection of the visible light reflected by the object;
   capturing, via a fluorescence image detector, a fluorescence image of the object via detection of fluorescence generated by the object responsive to the laser light;
   modulating, at a radio frequency, an intensifier of the fluorescence image detector with as few as three phase delays relative to the modulation of the laser light source;
   merging the fluorescence image and the visible light image to generate an intraoperative image showing an outline of a region of interest identified in the fluorescence image overlaid on the visible light image; and
   eliminating non-modulated, visible light from fluorescence images to produce a high contrast fluorescent image using the fluorescence images acquired with the as few as three phase delays.

8. The method of claim 7, wherein the phase delays comprise delays of zero degrees, 90 degrees and 180 degrees.

9. The method of claim 7, wherein each of the phase delays shifts phase of a radio frequency signal that modulates the intensifier by 90 degrees.

10. The method of claim 7, further comprising merging the high contrast fluorescent image and the visible light image to generate the intraoperative image.

11. The method of claim 7, further comprising:
extracting amplitude information from fluorescence images generated at each of the phase delays;
applying a threshold to the amplitude information; and
identifying edges of a structure based on the amplitude information above the threshold.

12. The method of claim 11, further comprising:
extracting a region of interest corresponding to the identified structures from the visible light image; and
merging the edges of the structure with the region of interest extracted from the visible light image.

13. Apparatus for intraoperative fluorescence imaging, comprising:
a radio frequency (RF) oscillator;
a phase shifter coupled to an output of the RF oscillator;
a white light source;
a visible light image detector;
a laser light source coupled to the RF oscillator, wherein RF signal generated by the RF oscillator modulates laser light generated by the laser light source;
a fluorescence image detector comprising an intensifier, wherein the intensifier is coupled to the phase shifter and phase shifted RF signal output by the phase shifter modulates the intensifier;
a control and image acquisition system coupled to the visible light image detector and to the fluorescence image detector, and configured to:
set the phase shifter to modulate the intensifier of the fluorescence image detector with as few as three phase delays relative to the modulation of the laser source per intraoperative image;
set each successive phase delay to advance phase of the RF signal that modulates the intensifier by 90 degrees;
eliminate non-modulated, visible light from fluorescence images to produce a high contrast fluorescent image using the fluorescence images acquired with the as few as three phase delays; and
merge the high contrast fluorescence image and a visible light image produced by the visible light image detector to generate an intraoperative image showing an outline of a region of interest identified in the fluorescence image overlaid on the visible light image.

14. The apparatus of claim 13, wherein the control and image acquisition system is configured to:
extract amplitude information from fluorescence images generated at each of the phase delays;
apply a threshold to the amplitude information; and
identify edges of a structure based on the amplitude information above the threshold;
extract a region of interest corresponding to the identified structures from the visible light image; and
merge the edges of the structure with the region of interest extracted from the visible light image.

15. A system for intraoperative fluorescence imaging, comprising:
a visible light illumination source;
a laser light source;
a visible light image detector;
a fluorescence image detector;
radio frequency (RF) circuitry coupled to the laser light source, the RF circuitry configured to modulate laser light generated by the laser light source with as few as two phase delays, wherein lasing current is below and above a lasing threshold of the laser light source; and
an image processing system coupled to the visible light image detector and to the fluorescence image detector, the image processing system configured to:
merge a fluorescence image produced by the fluorescence image detector and a visible light image produced by the visible light image detector to generate an intraoperative image showing an outline of a region of interest identified in the fluorescence image overlaid on the visible light image;
extract amplitude information from fluorescence images generated at each of the phase delays;
apply a threshold to the amplitude information; and
identify edges of a structure based on the amplitude information above the threshold.

16. The system of claim 15, wherein the image processing system is configured to eliminate non-modulated, visible light from fluorescence images to produce a high contrast fluorescent image using the fluorescence images acquired with the as few as two phase delays.

17. The system of claim 16, wherein the image processing system is configured to merge the high contrast fluorescent image and the visible light image to generate the intraoperative image.

18. The system of claim 15, wherein the image processing system is configured to:
extract a region of interest corresponding to the identified structures from the visible light image; and
merge the edges of the structure with the region of interest extracted from the visible light image.

19. A method for intraoperative fluorescence imaging, comprising:
illuminating an object with visible light generated by a visible light source;
illuminating the object with laser light generated by a laser light source;
modulating the laser light at a radio frequency with as few as two phase delays, wherein lasing current is below and above a lasing threshold of a laser light source generating the laser light;
capturing, via a visible light image detector, an image of the object via detection of the visible light reflected by the object;
capturing, via a fluorescence image detector, a fluorescence image of the object via detection of fluorescence generated by the object responsive to the laser light;
merging the fluorescence image and the visible light image to generate an intraoperative image showing an outline of a region of interest identified in the fluorescence image overlaid on the visible light image;
extracting amplitude information from fluorescence images generated at each of the phase delays;
applying a threshold to the amplitude information; and
identifying edges of a structure based on the amplitude information above the threshold.

20. The method of claim 19, further comprising eliminating non-modulated, visible light from fluorescence images to produce a high contrast fluorescent image using the fluorescence images acquired with the as few as two phase delays.

21. The method of claim 20, further comprising merging the high contrast fluorescent image and the visible light image to generate the intraoperative image.

22. The method of claim 19, further comprising:
extracting a region of interest corresponding to the identified structures from the visible light image; and
merging the edges of the structure with the region of interest extracted from the visible light image.

* * * * *